United States Patent [19]
Dorigatti et al.

[11] Patent Number: 5,879,359
[45] Date of Patent: Mar. 9, 1999

[54] BIODEGRADABLE GUIDE CHANNELS COMPRISED OF ESTERS OF HYALURONIC ACID FOR USE IN TISSUE REPAIR AS SURGICAL AIDS

[75] Inventors: Franco Dorigatti, Trento; Giorgio Favaro, Venzezia; Lanfranco Callegaro, Padua; Aurelio Romeo, Rome, all of Italy

[73] Assignee: Fidia S.p.A., Abano Terme, Italy

[21] Appl. No.: 855,285

[22] Filed: May 13, 1997

Related U.S. Application Data

[63] Continuation of Ser. No. 374,715, filed as PCT/EP93/02066 Aug. 3, 1993 published as WO94/03212 Feb. 17, 1994, abandoned.

[30] Foreign Application Priority Data

Aug. 3, 1992 [IT] Italy ................................. PD92A0144

[51] Int. Cl.⁶ ................................................... A61B 17/08
[52] U.S. Cl. ............................. 606/152; 606/154; 623/11
[58] Field of Search .................................. 606/151–156; 623/1, 11

[56] References Cited

U.S. PATENT DOCUMENTS

| | | |
|---|---|---|
| 4,534,349 | 8/1985 | Barrows . |
| 5,336,767 | 8/1994 | della Valle et al. ................... 536/55.1 |

FOREIGN PATENT DOCUMENTS

| | | |
|---|---|---|
| 8900431 | 1/1989 | WIPO . |
| 9005552 | 5/1990 | WIPO . |
| 9213579 | 8/1992 | WIPO . |
| 9311805 | 6/1993 | WIPO . |

OTHER PUBLICATIONS

Madison et al. (1988) *Brain Research* 447:325–334.
Favaro et al. (1990) *Trans. Am. Soc. Artif. Intern Organs*, vol. XXXVI:M291–294.
Meislin et al. (1990) *Journal of Applied Biomaterials* 1:13–19.
Williams et al. (1987) *The Journal of Comparative Neurology* 264:384–290.
Molander et al. (1982) *Muscle & Nerve* 5:54–57.
Nyilas et al., Trans Am. Soc. Artif. Intern Organs (1983) 29:307–313.
Yannas et al., 11th Ann. Meeting Soc. for Biomaterials (1985), p. 146.
Midgley et al., Univ. Surgical Clinics, McGill Univ. Faculty of Medicine, pp. 519–520.
Ducker et al., Dept. of Army, Div. of Surg., Washington, D.C., J. Neurosurg (1968), 28:582–587.
Lundborg et al., Journal of Neuropathology and Exp. Neurology (1982), vol. 41, No. 4, pp. 412–422.
Uzman et al., Journal of Neuroscience Research (1983), 9:325–338.

*Primary Examiner*—Robert A. Clarke
*Attorney, Agent, or Firm*—Birch, Stewart, Kolasch & Birch, LLP

[57] ABSTRACT

The present invention is drawn to medical devices comprising biodegradable guide channels for use in the repair and regeneration of nerve tissue. The guide channels of the present invention comprise interlaced threads imbedded in a matrix, wherein both the matrix and the threads comprise biocompatible and bioabsorbable esters of hyaluronic acid. The matrix of the present invention further optionally comprises biologically or pharmacologically active factors in association with the guide channels.

22 Claims, 5 Drawing Sheets

BIODEGRADABLE GUIDE CHANNELS COMPRISED OF ESTERS OF HYALURONIC ACID FOR USE IN TISSUE REPAIR AS SURGICAL AIDS

This application is a continuation of application Ser. No. 08/374,715 filed on Mar. 23, 1995, now abandoned, which is a 371 application of PCT/EP93/02066 filed Aug. 03, 1993 published as WO94/03212 Feb. 17, 1994.

BACKGROUND OF THE INVENTION

1. Field of the Invention

The present invention relates to biodegradable guide channels, processes for their preparation, and methods for their use in various surgical applications, specifically in the microsurgery of anatomical sites where conditions of discontinuity and/or loss of substance have occurred.

2. Description of Related Art

Research to identify alternative surgical techniques to treat, in particular, lesions to the peripheral nerves and various parts of the anatomy where conditions of discontinuity and/or loss of substance have occurred, such as in tendon surgery, has been described in the literature. Most of the studies performed so far have specifically focused on the treatment of trauma to the peripheral nerves, as described in more detail infra. However, special attention is now being paid to tendon surgery, for which the use of gelatin tubes, cellophane, or polyethylene structures, which give rise to rejection phenomena, have already been described. More recently, materials composed of regenerated, oxidized cellulose have been studied (Meislin R. J. et al., J. of Applied Biomaterials 1, 13–19, 1990).

A considerable part of such research has, however, been focused on the use of guide channels or tubular replacements for use as supports in the regeneration of damaged nerves in the treatment of trauma to the peripheral nerves.

These tubular replacements allow the two severed nerve ends to be held in proximity to each other, thus enabling the nerve to regenerate under suitable biological conditions. Moreover, these tubes inhibited or delayed the effects of infiltration linked with the connective tissue. Some guide channels or replacements made for these purposes with various polymers or their derivatives are already known (Ducker at al., Vol. 28, J. Neurosurg., 582–587, 1968; Midgley et al., Vol. 19, Surgical Forum, 519–528, 1968; Lundborg et al., Vol. 41, J. Neuropath. in Exp. Neurol., 412–422, 1982; Molander at al., Vol. 5, Muscle & Nerve, 54–58, 1982; Uzman at al., Vol. 9, J. Neurosci. Res. 325–338, 1983; Nyilas at al., Vol. 29, Transactions Am. Soc. Artif. Internal Organs, 307–313, 1983; and U.S. Pat. No. 4,534,349, 1985).

In order to increase functional recovery of the damaged nerve, tubular replacements have been prepared with biological polymers and mixtures of the same traditionally used in nerve repair (Madison et al., Vol. 44, Brain Res., 325–334, 1985; Yannas et al., Vol. 11, Trans. soc. Biomat. 146, 1985; Williams et al., Vol. 264, J. Comp. Neurol. 284–290, 1987). The possibility of including various growth factors in these tubular replacements has been studied (Politis at al., Vol. 253, Brain Res. 1–12, 1982; Aebischer at al., PCT WO 90/05552). The drawbacks of including growth factors in these tubular replacements by known methods is due to the fact that they are not stable in aqueous solutions, their half-lives are measured in hours rather than in weeks, the latter being the time necessary for complete nerve regeneration. Under these conditions, the release of these factors cannot be controlled, and they are often administered in the form of a bolus, which does not allow sufficiently long-lasting stimulation of the nerve cells required for regeneration.

A further step forward in the area of tubular replacements is represented by the preparation of polymers with which it is possible to make biocompatible and biodegradable replacements which remain in place according to the degree of chemical modification of the natural polymer and on the type of substitute used (Favaro G. et al., XXXVI Trans. Am. Soc. Artif. Organs, M291–M294, 1990). In this case too, the two nerve stumps are fixed within the tubular channel by sutures. Moreover, these materials have the added advantage of providing a guide for nerve regeneration, with the possibility of allowing the new growth to occur in the proper environment once the material used has been absorbed.

Various methods have been proposed for the preparation of guide channels with biocompatible and bioabsorbable materials. The most simple and rapid technique is the extrusion of a solution of biocompatible and bioabsorbable material through suitable holes.

Limitations on the use of guide channels made with some biocompatible and bioabsorbable materials, produced by extrusion or other manufacturing techniques, is their more or less marked tendency to tear when the nerve stumps are stitched to them.

There therefore exists a need for biocompatible and bioabsorbable guide channels with particular physicochemical and biological characteristics, particularly for those guide channels which contain specific trophic factors and/or compounds with bioactivity for a specific anatomical target, which permit then to be used to great advantage in surgery and microsurgery of the peripheral nerves or other anatomical areas in which conditions of discontinuity and/or loss of substance occur, and in which it is necessary to prevent the incidence and recurrence of post-operative adherences.

SUMMARY OF THE INVENTION

The present invention therefore provides guide channels of interlaced tubular membranes formed by a braiding technique, with valuable physicochemical and biological characteristics. By, virtue of the technological progress that has now been made, the new guide channels of the present invention can be made with particular resistances, much reduced thicknesses, and the possibility of varying the cross sections thereof. Moreover, these interlaced tubular membranes can contain biologically active molecules destined to be released during degradation of the tube, such as growth factors pharmacologically active on the peripheral nerves and/or any substances or compounds with specific bioactivity on the anatomical target of the guide channel.

The physicochemical and biological characteristics of the new guide channels can be used to great advantage in a wide variety of surgical and microsurgical situations at the level of the peripheral nerves and those anatomical zones where, thanks in particular to the physicochemical characteristics of the primary component of the tubes, the use of said guide channels can be highly advantageous owing to their ability to prevent the incidence and recurrence of post-surgical adherence, such as in tendon surgery.

Further scope of applicability of the present invention will become apparent from the detailed description and drawings provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed description taken in conjunction with the accompanying drawings, all of which are given by way of illustration only, and are not limitative of the present invention, in which.

DETAILED DESCRIPTION OF THE INVENTION

Figure 1:
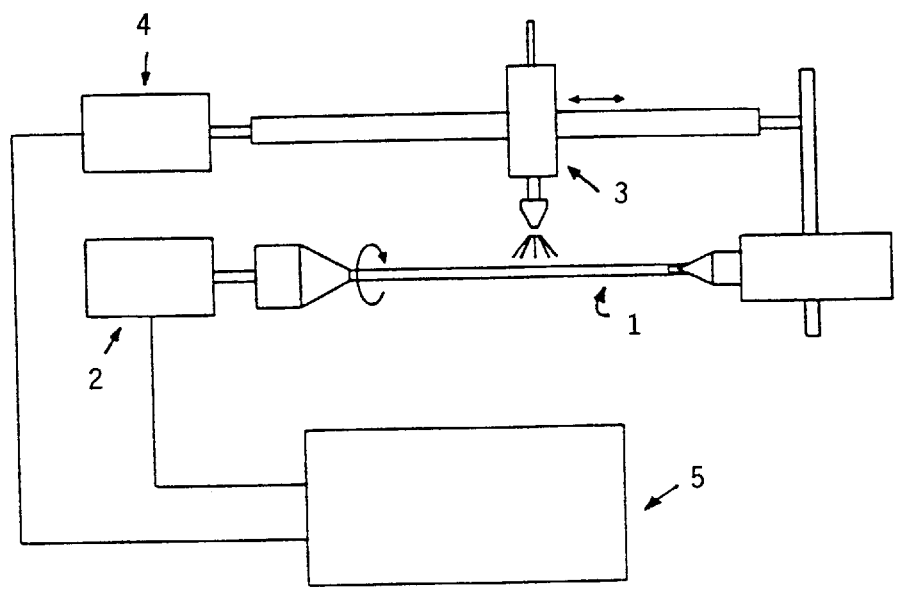
FIG. 1 is a schematic diagram of the apparatus used to prepare the composite guide channels of the present invention.

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The contents of each of the references cited herein are incorporated by reference in their entirety.

The guide channels according to the present invention comprise biocompatible and bioabsorbable materials measuring between about 5 and about 150 mm in length, preferably 20 mm, an internal diameter between about 1 and about 15 mm, preferably 1.5–3 mm, a thickness of between about 50 and about 1,000 μm, preferably 400 μm, and a weight between about 8 and about 80 mg, preferably 20 mg, corresponding to 4–40 mg/cm, preferably 10 mg/cm.

The guide channels are composed of a matrix of biocompatible and bioabsorbable material wherein a reinforcing tubular structure of a single thread or interlaced threads of the same or different biocompatible and bioabsorbable materials are embedded. The reinforcing structure, which serves as a defense against tears caused by suture threads or surgical needles and as a reinforcement, is composed of a thread produced by the usual methods of dry or wet extrusion and can be single ply or multiple, possibly twisted or combined with other threads made of other materials as long as they are also biocompatible and bioabsorbable.

This thread must have a minimum value of about 120 denier (UNI 8517/84), a minimum tensile strength at break of about 0.6 gr/denier, and a minimum elongation of about 3% (UNI 1932/86). The minimum number of threads making up the weave is about 8, the preferable number being 16, so that a particularly resistant structure is obtained. The denier of this thread can range from about 120 denier to about 600 denier; the tensile strength at break can range from about 0.6 gr/denier to about 3.5 gr/denier; the minimum elongation can range from about 3% to about 10%; and the number of threads making up the tubular weave can range from about 8 to about 16.

The matrix of biocompatible and bioabsorbable material totally covers the reinforcing tube. To modulate the thickness of the guide channel and to obtain a particularly fine product, the guide channel can be coated with the polymeric matrix by spraying. As discussed supra, both the tubular structure and the matrix comprise biocompatible and bioabsorbable materials.

These guide channels comprise semisynthetic materials derived from natural acidic polysaccharides such as semisynthetic derivatives of hyaluronic acid (HY), in particular ester derivatives of the same, as described in European patent publication No. 0216453 and U.S. Pat. No. 4,851,521. A characteristic that makes these materials particularly suitable for use according to the present invention is that they do not give rise to any rejection phenomena as they are not immunogenic, and do not cause any thrombotic effects. The guide channels of the present invention can be obtained both from total esters and from partial esters of hyaluronic acid, i.e., water-insoluble products with the notable advantage of forming products or biomaterials that are absorbable in the body (i.e., bioabsorbable) and which are degradable in the organism itself, becoming transformed into polymers that are present in nature (i.e., they are biocompatible). Such HY esters can be used to form both the tubular reinforcement structure as well as the surrounding polymeric matrix.

Moreover, biologically active molecules that can be used, if necessary, to make guide channels according to the present invention, are in particular those factors that increase or stimulate the regeneration, growth, and/or repair of damaged tissues. Indeed various factors that stimulate and enhance nervous regeneration are known (Wolicke et al., Vol. 83, Proc. Natl. Acad. Sci., U.S.A. 3012–3016, 1986; Rydel et al., Vol. 1, J. Neurosci. 3639–3653, 1988; Levi Montalcini; Vol. 237, Science, 1154–1162, 1987 and references cited therein; Brooker et al., Muscle and Nerve 13, 785–800, 1990).

Such growth factors include Nerve Growth Factor (NGF), Basic Fibroblast Growth Factor (FGF) in its acid or basic forms, Ciliary Keurotrophic Factor (CNTF), Brain Derived Nourotrophic Factor (BDNF), Neurotrophin-3 (NT-3), and Neurotrophin-4 (NT-4). Such growth factors can be obtained by recombinant DNA techniques, and can be used in truncated, chimeric, or monomeric forms.

Moreover, guide channels according to the present invention can contain compounds with specific bioactivity for the anatomical target where said guide channels are to be used, such as can occur in cases of guide channels for damaged nerves benefiting from the use of a structure containing molecules such as natural gangliosides or inner esters of said gangliosides, as described in EP 0072722, or ester or aside derivatives of gangliosides, as described in EP 0167449.

These biologically active molecules can be inserted in the guide channel by co-extrusion with the thread which comprises the reinforcing structure, or by solubilizing them in the matrix solution.

PREPARATION OF THE GUIDE CHANNELS OF THE PRESENT INVENTION

The guide channels of the present invention are produced by using the technique of interlacing threads to obtain a structure which is particularly resistant both to static and dynamic stress. According to the procedure used, the thread is wound onto bobbins which are suitable for use on the threading machine. The number of bobbins used varies between 8 and 16 according to the required resistance, weight, and size of the finished guide channel. The bobbins are fitted into place on the machine which is then switched on. The interwoven tubular product is then cut into 200 mm sections and placed on a steel bar (AISI 316 electropolished). This apparatus is represented by the diagram in FIG. 1.

Using the machine represented in FIG. 1, the steel bar with an interlaced tube fitted over it (1) is mounted on its axis and rotated by means of the motor (2). The polymeric matrix is applied either by spreading polymer solution over the rotating system and subsequently removing any excess, or by spraying the solution by means of the spray indicated as (3) which moves up and down the steel bar by means of a motor (4). This last system allows the thickness of the guide channel to be better controlled so that very thin guide channels can be made.

The motors are run by means of an automatic system (5).

For illustrative purposes only, described hereafter are some examples of the materials, apparatus, and processes useful in obtaining the guide channels according to the present invention.

The Esters of Hyaluronic Acid

Esters of hyaluronic acid useful in the present invention are esters of hyaluronic acid with aliphatic, araliphatic, cycloaliphatic or heterocyclic alcohols, in which are esterified all (so-called "total esters") or only a part (so-called "partial esters") of the carboxylic groups of the hyaluronic acid, and salts of the partial esters with metals or with organic bases, biocompatible or acceptable from a pharmacological point of view.

The useful esters are preferably esters which derive from alcohols which do not themselves possess a notable pharmacological action, such as, for example, the saturated alcohols of the aliphatic series or simple alcohols of the cycloaliphatic series.

In the above-mentioned esters in which some of the carboxylic acid groups remain free (i.e., partial esters), these may be salified with metals or organic bass, such as with alkaline or alkaline earth metals or with ammonia or nitrogenous organic bases.

Most of the esters of hyaluronic acid ("HY"), unlike HY itself, possess a certain degree of solubility in organic solvents. This solubility depends on the percentage of esterified carboxylic groups and on the type of alkyl group linked with the carboxyl. Therefore, an HY compound with all its carboxylic groups esterified possesses, at room temperature, good solubility in, for example, dimethylsulfoxide (the benzyl ester of HY dissolves in DMSO at 200 mg/ml). Most of the total esters of HY also possess, unlike HY and especially its salts, poor solubility in water, and are essentially insoluble in water. The solubility characteristics, together with particular and notable viscoelastic properties, make the HY esters particularly preferred for use as nerve guide channels.

Alcohols of the aliphatic series to be used as esterifying components of the carboxylic groups of hyaluronic acid for use as guide channels according to the present invention are, for example, those with a maximum of 34 carbon atoms, which may be saturated or unsaturated, and which may possibly also be substituted by other free functional or functionally modified groups, such as amine, hydroxyl, aldehyde, ketone, mercaptan, or carboxyl groups, or by groups derived from these, such as hydrocarbyl or di-hydrocarbylamine groups (the term "hydrocarbyl" will be used to refer not only to monovalent radicals of hydrocarbons such as the $C_nH_{2n+1}$ type, but also bivalent or trivalent radicals, such as "alkylenes" ($C_nH_{2n}$) or "alkylidenes" ($C_nH_{2n}$), ether or ester groups, acetal or ketal groups, thioether or thioester groups, and esterified carboxyl or carbamide groups and carbamide substituted by one or more hydrocarbyl groups, by nitrile groups, or by halogens.

Of the above-mentioned groups containing hydrocarbyl radicals, these are preferably lower aliphatic radicals, such as alkyls, with a maximum of 6 carbon atoms. Such alcohols may also be interrupted in the carbon atom chain by heteroatoms, such as oxygen, nitrogen, and sulfur atoms. Preferred are alcohols substituted with one or two of the said functional groups.

Alcohols of the above-mentioned group which are preferably used are those with a maximum of 12, and especially 6 carbon atoms, and in which the hydrocarbyl atoms in the above-mentioned amine, ether, ester, thioether, thioester, acetal, or ketal groups represent alkyl groups with a maximum of 4 carbon atoms. In the esterified carboxyl or substituted carbamide groups, the hydrocarbyl groups are alkyls with the same number of carbon atoms, and in which in the amine or carbamide groups may be alkylenamine or alkylencarbamide groups with a maximum of 8 carbon atoms. Of these alcohols, specifically preferred are saturated and non-substituted alcohols, such as the methyl, ethyl, propyl, and isopropyl alcohols, normal butyl alcohol, isobutyl alcohol, tertiary butyl alcohol, the amyl, pentyl, hexyl, octyl, nonyl and dodecyl alcohols and, above all, those with a linear chain, such as normal octyl and dodecyl alcohols. Of the substituted alcohols of this group, the bivalent alcohols are useful, such as ethyleneglycol, propyleneglycol and butyleneglycol, the trivalent alcohols such as glycerine, the aldehyde alcohols such as tartronic alcohol, the carboxylic alcohols such as lactic acids, for example glycolic acid, malic acid, the tartaric acids, citric acid, the aminoalcohols, such as normal aminoethanol, aminopropanol, normal aminobutanol and their dimethylated and diethylated derivatives in the amine function, choline, pyrrolidinylethanol, piperidirylethanol, piperazineylethianol and the corresponding derivatives of normal propyl or normal butyl alcohol, monothioethyleneglycol or its alkyl derivatives, such as the ethyl derivative in the mercaptan function.

Of the higher saturated aliphatic alcohols, preferred are cetyl alcohol and myricyl alcohol, but for the aim of the present invention, the higher unsaturated alcohols with one or two double bonds are especially important, such as especially those contained in many essential oils and with affinity to terpene, such as citronellol, geraniol, nerol, nerolidol, linalool, farnesol, and phytol. Of the unsaturated lower alcohols it is necessary to consider allyl alcohol and propargyl alcohol. Of the aralipathic alcohols, preferred are those with only one benzene residue and in which the aliphatic chain has a maximum of 4 carbon atoms, in which the benzene residue can be substituted by between 1 and 3 methyl or hydroxyl groups or by halogen atoms, especially by chlorine, bromine and iodine, and in which the aliphatic chain may be substituted by one or more functions selected from the group consisting of free amine groups or mono- or dimethylated amine groups, or by pyrrolidine or piperidine groups. Of these alcohols, most preferred are benzyl alcohol and phenetyl alcohol.

The alcohols of the cycloaliphatic or aliphatic-cycloaliphatic series may derive from mono- or polycyclic hydrocarbons, may preferably have a maximum of 34 carbon atoms, may be unsubstituted, and may contain one or more substituents, such as those mentioned above for the aliphatic alcohols. Of the alcohols derived from cyclic monoannular hydrocarbons, preferred are those with a maximum of 12 carbon atoms, the rings with preferably between 5 and 7 carbon atoms, which may be substituted, for example, by between one and three lower alkyl groups, such as methyl, ethyl, propyl or isopropyl groups. As specific alcohols of this group, the following are most preferred: cyclohexanol, cyclohexanediol, 1,2,3-cyclohexanetroil and 1,3,5-cyclohexanetriol (phloroglucitol), inositol, and the alcohols which derive from p-methane such as carvomenthol, menthol, and α-γterpineol, 1-terpineol, 4-terpineol and piperitol, or the mixture of these alcohols known as "terpineol", 1,4-, and 1,8-terpin. Of the alcohols which derive from hydrocarbons with condensed rings, such as thujane, pinane or comphane, the following are preferred: thujanol, sabinol, pinol hydrate, D- and L-borneol, and D- and L-isoborneol.

METHOD OF PREPARING THE PRESENT INVENTION

Method A:

The esters of hyaluronic acid may be prepared by methods known per se for the esterification of carboxylic acids, for example by treatment of free hyaluronic acid with the desired alcohols in the presence of catalyzing substances, such as strong inorganic acids or ionic exchangers of the acid type, or with an etherifying agent capable of introducing the desired alcoholic residue in the presence of inorganic or organic bases. As esterifying agents, it is possible to use those known in the literature, such as especially the esters of various inorganic acids or of organic sulfonic acids, such as hydracids, that is hydrocarbyl halogenides, such as methyl or ethyl iodide, or neutral sulphates or hydrocarbyl acids, sulfites, carbonates, silicates, phosphates or hydrocarbyl sulfonates, such as methyl benzene or p-toluene-sulfonate or methyl or ethyl chlorosulfonate. The reaction may take place in a suitable solvent, for example an alcohol, preferably that corresponding to the alkyl group to be introduced in the carboxyl group. But the reaction may also take place in non-polar solvents, such as ketones, ethers, such as dioxane, cr aprotic solvents, such as dimethylsulfoxide. As a base it is possible to use, for example, a hydrate of an alkaline or alkaline earth metal or magnesium or silver oxide or a basic salt or one of these metals, such as a carbonate, and, of the organic bases, a tertiary azotized base, such as pyridine or collidine. In the place of the base it is also possible to use an ionic exchanger of the basic type.

Another esterification method employs the metal salts or salts with organic azotized bases, for example ammonium or ammonium substitute salts. Preferably, salts of the alkaline or alkaline earth metals are used, but any other metallic salt may be used. The esterifying agents are also in this case those mentioned above and the same applies to the solvents. It is preferable to use aprotic solvents, for example dimethylsulfoxide and dimethylformamide.

In the esters obtained according to this procedure or according to the procedure described hereafter, free carboxylic groups of the partial esters may be salified, if desired, in a per se known manner.

Method B:

The hyaluronic esters may also be prepared by a method which consists of treating a quaternary ammonium salt of hyaluronic acid with an etherifying agent, preferably in an aprotic organic solvent.

As organic solvents, it is preferable to use aprotic solvents, such as dialkylsulfoxides, dialkylcarboxamides, such as in particular lower alkyl dialkylsulfoxides, especially dimethylsulfoxide, and lower alkyl dialkylamidea of lower aliphatic acids, such as dimethyl- or diethylformamide or dimethyl- or diethylacetamide.

Other solvents, however, are to be considered which are not always aprotic, such as alcohols, ethers, ketones, esters, especially aliphatic or heterocyclic alcohols and ketones with a lower boiling point, such as hexafluoroisopropanol, trifluoroethanol, and N-methylpyrrolidone.

The reaction is effected preferably in a temperature range of between about 0° C. and 100° C., especially between about 25° C. and 75° C., for example at about 30° C.

The esterification is carried out preferably by adding by degrees the esterifying agent to the above-mentioned ammonium salt to one of the above mentioned solvents, for example to dimethylsulfoxide.

As an alkylating agent it is possible to use those mentioned above, especially the hydrocarbyl halogens, for example alkyl halogens. As starting quaternary ammonium salts, it is preferable to use the lower ammonium tetraalkylates, with alkyl groups preferably between 1 and 6 carbon atoms. Mostly, hyaluronate of tetrabutylammonium is used. It is possible to prepare these quaternary ammonium salts by reacting a metallic salt of hyaluronic acid, preferably one of those mentioned above, especially the sodium or potassium salt, in aqueous solution with a salified sulfonic resin with a quaternary ammonium base.

One variation of the previously described procedure consists of reacting a potassium or sodium salt of hyaluronic acid, suspended in a suitable solution such as dimethylsulfoxide, with a suitable alkylating agent in the presence of catalytic quantities of a quaternary ammonium salt, such as iodide of tetrabutylammonium.

For the preparation of the hyaluronic acid esters, it is possible to use hyaluronic acids of any origin, such as for example the acids extracted from natural starting materials, for example from cocks' combs. The preparation of such acids is described in the literature; preferably, purified hyaluronic acids are used. Especially used are hyaluronic acids comprising molecular fractions of the integral acids obtained directly by extraction of the organic materials with molecular weights varying within a wide range, for example from about 90%–80% (MW=11.7 to 10.4 million) to 0.2% (MW=30,000) of the molecular weight of the integral acid having a molecular weight of 13 million, preferably between 5% and 0.2%. Such fractions may be obtained by various procedures described in literature, such as by hydrolytic, oxidative, enzymatic, or physical procedures, such as mechanical or radiational procedures. Primordial extracts are therefore often formed during these same by publication procedures (for example see the article by Balazs et al. in "Cosmetics & Toiletries"). The separation and purification of the molecular fractions obtained are brought about by known techniques, for example by molecular filtration.

Additionally useful are purified fractions obtainable from hyaluronic acid, such as for example those described in European Patent Publn. No. 0138572.

The salification of HY with the above metals, for the preparation of starting salts for the particular esterification procedure described above, is performed in a per se known manner, for example by reacting HY with the calculated base quantity, for example with alkaline hydrates or with basic salts of such metals, such as carbonates or bicarbonates.

In the partial esters, it is possible to salify all the remaining carboxylic groups or only part of them, dosing the base quantities so as to obtain the desired stoichiometric degree of salification. With the correct degree of salification, it is possible to obtain esters with a wide range of different dissociation constants and which therefore give the desired pH in solution or in situ at the time of therapeutic application.

PREPARATION EXAMPLES

The following exemplify the preparation of hyaluronic acid esters useful in the guide channels of the present invention.

Example 1

Preparation of the (Partial) Propyl Ester of Hyaluronic Acid (HY)—50% Esterified Carboxylic Groups,—50% Salified Carboxylic Groups (Na)

12.4 g of HY tetrabutylammonium salt with a molecular weight of 170,000, corresponding to 20 m.Eq. of a monomeric unit, are solubilized in 620 ml of dimethylsulfoxide at 25° C. 1.8 g (10.6 m.Eq.) of propyl iodide are added and the resulting solution is kept at a temperature of 30° for 12 hours.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water, 5:1, and three times with acetone, and finally vacuum dried for eight hours at 30° C.

The product is then dissolved in 550 ml of water containing 1% sodium chloride and the solution is slowly poured into 3,000 ml of acetone under constant agitation. A precipitate is formed which is filtered and washed twice with 500 ml of acetone/water, 5:1, three times with 500 ml of acetone, and finally vacuum dried for 24 hours at 30° C. 7.9 g of the partial propyl ester compound in the title are obtained. Quantitative determination of the ester groups is carried out using the method of R. H. Cundiff and P. C. Markunas [Anal. Chem. 33, 1028–1030, (1961)].

Example 2

Preparation of the (Partial) Isopropyl Ester of Hyaluronic Acid (HY)—50% Esterified Carboxylic Groups—50% Salified Carboxylic Groups (Na)

12.4 g of HY tetrabutylamnmoniumn salt with a molecular weight of 160,000, corresponding to 20 m.Eq. of a monomeric unit, are solubilized in 620 ml of dimeothylsulfoxide at 25° C. 1.8 g (10.6 m.Eq.) of isopropyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water, 5:1, and three times with acetone, and finally vacuum dried for eight hours at 30° C.

The product is then dissolved in 550 ml of water containing 1% sodium chloride and the solution is slowly poured into 3,000 ml of acetone under constant agitation. A precipitate is formed which is filtered and washed twice with 500 ml of acetone/water, 5:1, and three times with 500 ml of acetone, and finally vacuum dried for 24 hours at 30° C. 7.8 g of the partial isopropyl ester compound in the title are obtained. Quantitative determination of the ester groups is carried out using the method of R. H. Cundiff and P. C. Markunas [Anal. Chem. 33, 1028–1030 (1961)].

Example 3

Preparation of the (Partial) Ethyl Ester of Hyaluronic Acid (HY)—75% Esterified Carboxylic Groups—25% Salified Carboxylic Groups (Na)

12.4 g of HY tetrabutylammonium salt with a molecular weight of 250,000, corresponding to 20 m.Eq. of a monomeric unit, are solubilized in 620 ml of dimethylsulfoxide at 25° C. 2.5 g (15.9 m.Eq.) of ethyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water, 5:1, and three times with acetone, and finally vacuum dried for eight hours at 30° C.

The product is then dissolved in 550 ml of water containing 1% sodium chloride and the solution is slowly poured into 3,000 ml of acetone under constant agitation. A precipitate is formed which is filtered and washed twice with 500 ml of acetone/water, 5:1, and three times with 500 ml of acetone, and finally vacuum dried for 24 hours at 30° C. 7.9 g of the partial ethyl ester compound in the title are obtained. Quantitative determination of the ester groups is carried out using the method of R. H. Candiff and P. C. Markunas [Anal. Chem. 33, 1028–1030, (1961)].

Example 4

Preparation of the (Partial) Methyl Ester of Hyaluronic Acid (HY)—75% Esterified Carboxylic Groups—25% Salified Carboxylic Groups (Na)

12.4 g of HY tetrabutylammonium salt with a molecular weight of 80,000, corresponding to 20 m.Eq. of a monomeric unit, are solubilized in 620 ml of dimethylsulfoxide at 25° C. 2.26 g (15.9 m.Eq.) of methyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water, 5:1, and three times with acetone, and finally vacuum dried for eight hours at 30° C.

The product is then dissolved in 550 ml of water containing 1% sodium chloride and the solution is slowly poured into 3,000 ml of acetone under constant agitation. A precipitate is formed which is filtered and washed twice with 500 ml of acetone/water, 5:1, and three times with 500 ml of acetone and finally vacuum dried for 24 hours at 30° C. 7.8 g of the partial methyl ester compound in the title are obtained. Quantitative determination of the ester groups is carried out using the method of R. H. Cundiff and P. C. Markunas [Anal. Chem. 33, 1028–1030 (1961)].

Example 5

Preparation of the Methyl Ester of Hyaluronic Acid (HY)

12.4 g of HY tetrabutylammonium salt with a molecular weight of 120,000, corresponding to 20 m.Eq. of a monomeric unit, are solubilized in 620 ml of dimethylsulfoxide at 25° C. 3.3 g (21.2 m.Eq.) of methyl iodide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty four hours at 30° C.

8 g of the ethyl ester product in the title are obtained. Quantitative determination of the ester groups is carried out using the method of R. H. Cundiff and P. C. Markunas [Anal. Chem. 2, 1028–1030 (1961)].

Example 6

Preparation of the Ethyl Ester of Hyaluronic Acid (HY)

12.4 g of HY tetrabutylammonium salt with a molecular weight of 85,000, corresponding to 20 m.Eq. of a monomeric unit, are solubilized in 620 ml of dimethylsulfoxide at 25° C. 3.3 g (21.2 m.Eq.) of ethyl iodide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty-four hours at 30° C.

8 g of the ethyl ester product in the title are obtained. Quantitative determination of the ester groups is carried out using the method of R. H. Cundiff and P. C. Markunas [Anal. Chem. 33, 1028–1030 (1961)].

Example 7

Preparation of the Propyl Ester of Hyaluronic Acid (HY)

12.4 g of HY tetrabutylammonium salt with a molecular weight of 170,000, corresponding to 20 m.Eq. of a monomeric unit, are solubilized in 620 ml of dimethylsulfoxide at 25° C. 3.6 g (21.2 m.Eq.) of propyl iodide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty-four hours at 30° C.

8.3 g of the propyl ester product in the title are obtained. Quantitative determination of the ester groups is carried out using the method of R. H. Cundiff and P. C. Markunas [Anal. Chem. 22, 1028–1030 (1961)].

Example 8

Preparation of the (Partial) Butyl Ester of Hyaluronic Acid (HY)—50% Esterified Carboxylic Groups—50% Salified Carboxylic Groups (Na)

12.4 g of HY tetrabutylammonium salt with a molecular weight of 620,000, corresponding to 20 m.Eq. of a monomeric unit, are solubilized in 620 ml of dimethylsulfoxide at 25° C. 1.95 g (10.6 m.Eq.) of n-butyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water, 5:1, and three times with acetone and finally vacuum dried for eight hours at 30° C.

The product is then dissolved in 550 ml of water containing 1% sodium chloride and the solution is slowly poured into 3,000 ml of acetone under constant agitation. A precipitate is formed which is filtered and washed twice with 500 ml of acetone/water, 5:1, and three times with 500 ml of acetone, and finally vacuum dried for 24 hours at 30° C. 8 g of the partial butyl ester compound in the title are obtained. Quantitative determination of the ester groups is carried out using the method of R. H. Cundiff and P. C. Markunas [Anal. Chem. 33, 1028–1030 (1961)].

Example 9

Preparation of the (Partial) Ethoxycarbonylmethyl Ester of Hyaluronic Acid (HY)—75% Esterified Carboxylic Groups—25% Salified Carboxylic Groups (Na)

12.4 g of HY tetrabutylammonium salt with a molecular weight of 180,000, corresponding to 20 m.Eq. of a monomeric unit, are solubilized in 620 ml of dimethylsulfoxide at 25° C. 2 g of tetrabutylammonium iodide and 1.84 g (15 m.Eq.) of ethyl chloroacetate are added and the resulting solution of kept for 24 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water, 5:1, and three times with acetone, and finally vacuum dried for eight hours at 30° C.

The product is then dissolved in 550 ml of water containing 1% sodium chloride and the solution is slowly poured into 3,000 ml of acetone under constant agitation. A precipitate is formed which is filtered and washed twice with 500 ml of acetone/water, 5:1, and three times with 500 ml of acetone, and finally vacuum dried for 24 hours at 30° C. 10 g of the partial ethoxycarbonyl methyl ester compound in the title are obtained.

Quantitative determination of the ethoxylic ester groups is carried out using the method of R. H. Cundiff and P. C. Markunas [Anal. Chem. 33, 1028–1030 (1961)].

Example 10

Preparation of the n-pentyl Ester of Hyaluronic Acid (HY)

12.4 g of HY tetrabutylammonium salt with a molecular weight of 620,000, corresponding to 20 m.Eq. of a monomeric unit, are solubilized in 620 ml of dimethylsulfoxide at 25° C. 3.8 g (25 m.Eq.) of n-pentyl bromide and 0.2 g of iodide tetrabutylammoniumn are added, and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty four hours at 30° C.

8.7 g of the n-pentyl ester product in the title are obtained. Quantitative determination of the ester groups is carried out using the method described on pages 169–172 of Siggia S. and Hann J. G., "Quantitative Organic Analysis Via Functional Groups," 4th Edition, John Wiley and Sons.

Example 11

Preparation of the Isopentyl Ester of Hyaluronic Acid (HY)

12.4 g of HY tetrabutylammonium salt with a molecular weight of 170,000, corresponding to 20 m.Eq. of a monomeric unit, are solubilized in 620 ml of dimethylsulfoxide at 25° C. 3.8 g (25 m.Eq.) of isopentyl bromide and 0.2 g of tetrabutylamonium iodide are added, and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty four hours at 30° C.

8.6 g of the isopentyl ester product featured in the title are obtained. Quantitative determination of the ester groups is carried out according to the method described on pages 169–172 of Siggia S. and Hanna J. G., "Quantitative Organic Analysis Via Functional Groups," 4th Edition, John Wiley and Sons.

Example 12

Preparation of the Benzyl Ester of Hyaluronic Acid (HY)

12.4 g of HY tetrabutylammonium salt with a molecular weight of 170,000, corresponding to 20 m.Eq. of a monomeric unit, are solubilized in 620 ml of dimethylsulfoxide at 25° C. 4.5 g (25 m.Eq.) of benzyl bromide and 0.2 g of tetrabutylammonium iodide are added, and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty four hours at 30° C.

9 g of the benzyl ester product in the title are obtained. Quantitative determination of the ester groups is carried out according to the method described on pages 169–172 of Siggia S. and Hanna J. G. "Quantitative Organic Analysis via Functional Groups," 4th Edition, John Wiley and Sons.

Example 13

Preparation of the β-phenylethyl Ester of Hyaluronic Acid (HY)

12.4 g of HY tetrabutylammonium salt with a molecular weight of 125,000, corresponding to 20 m.Eq. of a monomeric unit, are solubilized in 620 ml of dimethylsulfoxide at 25° C. 4.6 g (25 m.Eq.) of 2-bromoethylbenzene and 185 mg of tetrabutylammonium iodide are added, and the solution is kept for 12 hours at 30° C.

The resulting mixture is slowly poured into 3,500 ml of ethyl acetate under constant agitation. A precipitate is thus formed which is then filtered and washed four times with 500 ml of ethyl acetate and finally vacuum dried for twenty four hours at 30° C.

9.1 g of the β-phenylethyl ester in the title are obtained. Quantitative determination of the ester groups is carried out according to the method described on page 168–172 of Siggia S. and Hanna J. G., "Quantitative Organic Analysis Via Functional Groups," 4th Edition, John Wiley and Sons.

Example 14

Preparation of the Benzyl Ester of Hyaluronic Acid (HY)

3 g of the potassium salt of HY with a molecular weight of 162,000 are suspended in 200 ml of dimethylsulfoxide; 120 mg of tetrabutylammonium iodide and 2.4 g of benzyl bromide are added.

The suspension is kept in agitation for 48 hours at 30° C. The resulting mixture is slowly poured into 1,000 ml of ethyl acetate under constant agitation. A precipitate is formed which is filtered and washed four times with 150 ml of ethyl acetate and finally vacuum dried for twenty four hours at 30° C.

3.1 g of the benzyl ester product in the title are obtained. Quantitative determination of the ester groups is carried out according to the method described on pages 169–172 of Siggia S. and Hanna J. G. "*Quantitative organic Analysis Via Functional Groups," 4th Edition, John Wiley and Sons.

Example 15

Preparation of Partial Benzyl Esters (HYAFF 11 p10, p25, p50, and p75) of Hyaluronic Acid The partial benzyl esters of hyaluronic acid, HYAFF 11 p10, p25, p50, and p75, can be prepared as described in Method B, supra. The esterification can be carried out by adding by degrees the esterifying agent to the quaternary ammonium salt of hyaluronic acid treated with an etherifying agent in the appropriate organic solvent.

The salification of hyaluronic acid for the preparation of starting salts for esterification and the salification of the remaining carboxyl groups in the partial benzyl esters is also describe in Method B.

Example 16

Preparation of the (Partial Propyl) ester of Hyaluronic Acid (HY)—85% esterified Carboxylic Groups—15% Salified Carboxylic Groups (Na)

12.4 g of HY tetrabutylammonium salt with a molecular weight of 165,000, corresponding to 20 m.Eq. of a monomeric unit, are solubilized in 620 ml of dimethylsulfoxide at 25° C. 2.9 g (17 m.Eq.) of propyl iodide are added and the resulting solution is kept for 12 hours at 30° C.

A solution is then added containing 62 ml of water and 9 g of sodium chloride and the resulting mixture is slowly poured into 3,500 ml of acetone under constant agitation. A precipitate is formed which is filtered and washed three times with 500 ml of acetone/water, 5:1, and three times with acetone, and finally vacuum dried for eight hours at 30° C.

The product is then dissolved in 550 ml of water containing 1% sodium chloride and the solution is slowly pouted into 3,000 ml of acetone under constant agitation. A precipitate is formed which is filtered and washed twice with 500 ml of acetone/water, 5:1, and three times with 500 ml of acetone, and finally vacuum dried for 24 hours at 30° C. 8 g of the partial propyl ester compound in the title are obtained. Quantitative determination of the ester groups is carried cut using the method of R. H. Cundiff and P. C. Markunas [Anal. Chem. 33, 1028–1030(1961)].

Example 17

Preparation of the n-octyl Ester of Hyaluronic Acid (HY)

12.4 g of HY tetrabutylammonium salt with a molecular weight of 170,000, corresponding to 20 m.Eq. of a monomeric unit, are solubilized in 620 ml of dimethylsulfoxide at 25° C. 4.1 g (21.2 m.Eq.) of 1-bromooctane are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.3 g of the octyl ester product in the title are obtained. Quantitative determination of the ester groups is carried out using the method described in Siggia S. and Hanna J. G., "Quantitative Organic Analysis Via Functional Groups," 4th Edition, John Wiley and Sons, pages 169–172.

Example 18

Preparation of the Isopropyl Ester of Hyaluronic Acid (HY)

12.4 g of HY tetrabutylammonium salt with a molecular weight of 170,000, corresponding to 20 m.Eq. of a monomeric unit, are solubilized in 620 ml of dimethylsulfoxide at 25° C. 2.6 g (21.2 m.Eq.) of isopropyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 8.3 g of the isopropyl ester product in the title are obtained. Quantitative determination of the ester groups is carried out using the method of R. H. Cundiff and P. C. Markunas (Anal. Chem. 33, 1028–1030, 1961).

Example 19

Preparation of the 2,6-dichlorobenzyl Ester of Hyaluronic Acid (HY)

12.4 g of HY tetrabutylammonium salt with a molecular weight of 170,000, corresponding to 20 m.Eq. of a monomeric unit, are solubilized in 620 ml of dimethylsulfoxide at 25° C. 5.08 g (21.2 m.Eq.) of 2,6-dichlorobenzyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.7 g of the 2,6-dichlorobenzyl ester product in the title are obtained. Quantitative determination of the ester groups is carried out using the method described fin Siggia S. and Hanna J. G., "Quantitative Organic Analysis Via Functional Groups," 4th Edition, John Wiley and Sons, pages 169–172.

Example 20

Preparation of the 4-terbutylbenzyl Ester of Hyluronic Acid (HY)

12.4 g of HY tetrabutylammonium salt with a molecular weight of 170,000, corresponding to 20 m.Eq. of a monomeric unit, are solubilized in 620 ml of dimethylsulfoxide at 25° C. 4.81 g (21.2 m.Eq.) of 4-terbutylbenzyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.8 g of the 4-terbutylbenzyl ester product in the title are obtained. Quantitative determination of the ester groups is carried out using the method described in Siggia S. and Hanna J. G., "Quantitative Organic Analysis Via Functional Groups," 4th Edition,, John Wiley and Sons, pages 169–172.

Example 21

Preparation of the Heptadecyl Ester of Hyaluronic Acid (HY)

12.4 g of HY tetrabutylammonium salt with a molecular weight of 170,000, corresponding to 20 m.Eq. of a monomeric unit, are solubilized in 620 ml of dimethylsulfoxide at 25° C. 6.8 g (21.2 M.Eq.) of heptadecyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 11 g of the heptadecyl ester product in the title are obtained. Quantitative determination of the ester groups is carried out using the method described in Siggia S. and Hanna J. G., "Quantitative organic Analysis Via Functional Groups," 4th Edition, John Wiley and Sons, pages 169–172.

Example 22

Preparition of the Octadecyl Ester of Hyaluronic Acid (HY)

12.4 g of HY tietrabutylanmonium salt with a molecular weight of 170,000, corresponding to 20 m.Eq. of a monomeric unit, are solubilized in 620 ml of dimethylsulfoxide at 25° C. 7.1 g (21.2 m.Eq.) of octadecyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 11 g of the Heptadecyl ester product in the title are obtained. Quantitative determination of the ester groups is carried out using the method described in Siggia S. and Hanna J. G., "Quantitative Organic Analysis Via Functional Groups," 4th Edition, John Wiley and Sons, pages 169–172.

Example 23

Preparation of the 3-phenylpropyl Ester of Hyaluronic Acid (HY)

12.4 g of HY tetrabutylammonium salt with a molecular weight of 170,000, corresponding to 20 m.Eq. of a monomeric unit, are solubilized in 620 ml of dimethylsulfoxide at 25° C. 4.22 g (21.2 m.Eq.) of 3-phenylpropyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9 g of the 3-phenylpropyl ester product in the title are obtained. Quantitative determination of the ester groups is carried out using the method described in Siggia S. and Hanna J. G., "Quantitative Organic Analysis via Functional Groups," 4th Edition, John Wiley and Sons, pages 169–172.

Example 24

Preparation of the 3,4,5-trimethoxy-benzyl Ester of Hyaluronic Acid (HY)

12.4 g of HY tetrabutylammonim salt with a molecular weight of 170,000, corresponding to 20 M.Eq. of a monomeric unit, are solubilized in 620 ml of dimethylsulfoxide at 25° C. 4.6 g (21.2 m.Eq.) of 3,4,5-trimethoxybenzyl chloride are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 10 g of the 3,4,5-trimethoxybenzyl ester product in the title are obtained. Quantitative determination of the ester groups is carried out using the method described in Siggia S. and Hanna J. G., "Quantitative Organic Analysis Via Functional Groups," 4th Edition, John Wiley and Sons, pages 169-172.

Example 25

Preparation of the Cinnamyl Ester of Hyaluronic acid (HY)

12.4 g of HY tetrabutylammonium salt with a molecular weight of 170,000, corresponding to 20 m.Eq. of a monomeric unit, are solubilized in 620 ml of dimethylsulfoxide at 25° C. 4.2 g (21.2 m.Eq.) of cinnamyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.3 g of the cinnamyl ester product in the title are obtained. Quantitative determination of the ester groups is carried out using the method described in Siggia S. and Hanna J. G., "Quantitative Organic Analysis Via Functional Groups," 4th Edition, John Wiley and Sons, pages 169–172.

Example 26

Preparation of the Decyl Ester of Hyaluronic Acid (HY)

12.4 g of HY tetrabutylammonium salt with a molecular weight of 170,000, corresponding to 20 m.Eq. of a monomeric unit, are solubilized in 620 ml of dimethylsulfoxide at 25° C. 4.7 g (21.2 m.Eq.) of 1-bromodecane are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.5 g of the decyl ester product in the title are obtained. Quantitative determination of the ester groups is carried out using the method described in Siggia S. and Hanna J. G., "Quantitative Organic Analysis Via Functional Groups," 4th Edition, John Wiley and Sons, pages 169–172.

Example 27

Preparation of the Nonyl Ester of Hyaluronic Acid (HY)

12.4 g of HY tetrabutylammonium salt with a molecular weight of 170,000, corresponding to 20 m.Eq. of a monomeric unit, are solubilized in 620 ml of dimethylsulfoxide at 25° C. 4.4 g (21.2 m.Eq.) of 1-bromononane are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9 g of the nonyl ester product in the title are obtained. Quantitative determination of the ester groups is carried out using the method described in Siggia S. and Hanna J. G., "Quantitative organic Analysis Via Functional Groups," 4th Edition, John Wiley and Sons, pages 169–172.

BIOLOGICALLY ACTIVE FACTORS

The active factors usable in the guide channels of the present invention are particularly those factors which enhance, promote, or stimulate regeneration, growth or repair of nerve tissue. There are various factors known to stimulate and enhance nerve regeneration, described for example in Wolicke et al., Vol. 83, Proc. Natl. Acad. Sci., U.S.A. 3012–3016, 1986; Rydel et al., Vol. 1, J. Neurosci. 3639–3653, 1988; Levi Montalcini, Vol. 237, Science, 1154–1162, 1987, including the references therein; and Brooker et al., Muscle and Nerve 13, 785–800, 1990.

Important growth factors are: Nerve Growth Factor (NGF); Fibroblast Growth Factor (FGF) in its acid (a-FGF) or basic form (b-FGF); Ciliary Neurotrophic Factor (CNTF), Brain Derived Neurotrophic Factor (BDNF), and Neurotropin-3 (NT-3). There are also substances such as gangliosides or their synthetic and semisynthetic derivatives which promote or enance the biological activity of these growth factors (Vantini et al., Brain Res. 448, 252–258, 1988). Useful, for example, are naturally existing gangliosides, inner ester ganglioside derivatives, such as are described in EP Patent No. 0072722, and aster and amide derivatives of gangliosides, such as are described in EP Patent No. 0167449.

Moreover, the growth factors are preferably human active factors and can be produced by recombinant DNA techniques.

Example 28

Preparation of Ganglioside Mixture, Cronassial 1000 grams of infected bovine brain, ground and suspended in distilled water, are left in contact with 300 to 600 ml of acetone (ratio 1:5, weight/volume) for about 3 hours at room temperature with stirring. The solution is then centrifuged at 6000× g at a temperature of between 4° C. and 7° C. until precipitation is complete. The solvent is then eliminated and 180–350 ml of a mixture of methylene chloride/methahol/sodium hydroxide is added to the wet powder placed in a suitable glass container, and is left again under magnetic stirring for at least three hours at a temperature of between 30° C. and 35° C. It is finally left to cool, and then centrifuged for 20 minutes at 6000× g at +10° C. the liquid phase is filtered through a filtering funnel at a temperature of +4° C. A suitable amount of calcium chloride and acetone is added to the liquid, left under stirring for about 30 minutes, and centrifuged at 6000× g at +10° C. The precipitate (raw material 1) is finally allowed to dry overnight and then for 5 hours under high vacuum.

Recovered raw material 1 is resuspended in 10 to 18 ml of a mixture of water/chloroform/methanol. The pH is adjusted to about 12 with 5N NaOH. The mixture is heated to between 38° and 43° C. for from 4 to 8 hours and loft under stirring. At the end of this time, after being allowed to cool, it was neutralized with 6N HCl, and the required amount of water/n-butanol/chloroform is added. The mixture is then stirred for 15 to 30 minutes and left to stand for between 2 and 4 hours. Finally, the lower organic phase is discarded, acetone and sodium chloride are added to the remaining aqueous phases, and they are stirred for about 30 minutes and centrifuged for 20 minutes at 6000× g at +15° C. (raw material 2).

The product is dried in a high vacuum, resuspended in 6 to 15 ml absolute methanol, and then kept hot for about 2 hours while stirring the solution from time to time. The suspension is then quickly centrifuged at 6000× g and the supernatant is placed in a freezer for about 2 hours. The opalescent white solution is then centrifuged at 0° C. at 600× g and the precipitate is dried in a high vacuum. The product is gathered in 1N sodium hydroxide and left in contact with the solution for at least 1 hour at room temperature. Finally, the pH of the suspension is brought to an approximate pH value of 9 and dialyzed through a membrane having a molecular weight cutoff of 10 kd against a suitable volume of distilled water. A suitable amount of sodium chloride and acetone is added, and the dialysate is centrifuged at +5° C. at 6000× g., and then dried under high vacuum (finished product). The sample is taken up in 10 mM phosphate buffer, pH 7.2, and sterilized at +121° C. for 30 minutes to produce the finished, sterilized product.

Example 29

Preparation of Monosialoganglioside $GM_1$, Sygen

The monosialoganglioside is a biological substance obtained from bovine brain, having the following structural formula:

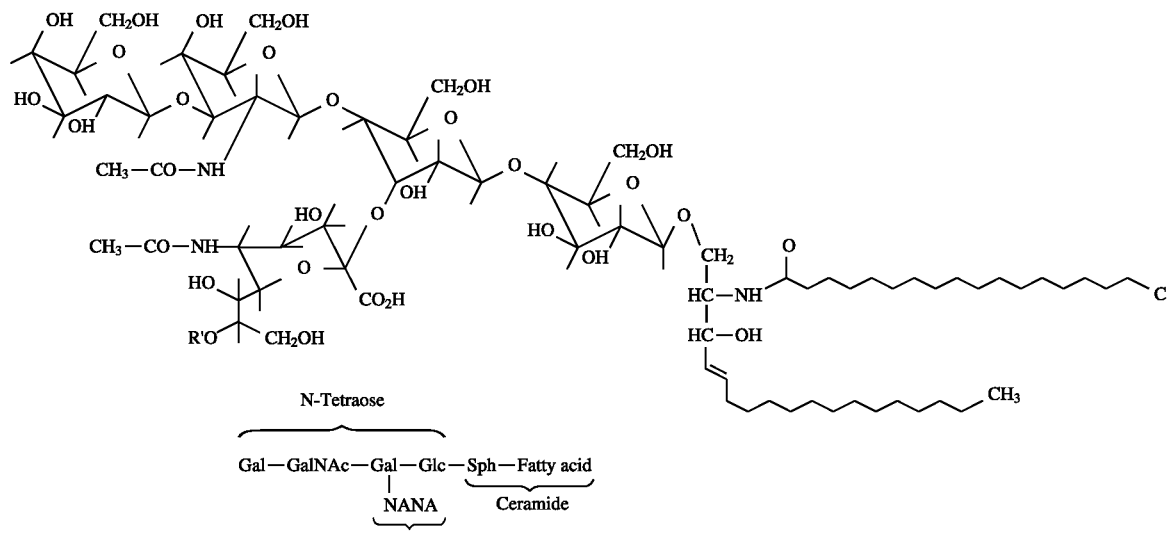

$C_{M1}$: R=R'=H $II^3$-alpha-NeuAc-GgOse$_4$Cer

The sodium salt of monosialotetrahexosylganglioside $GM_1$ can be isolated as a highly purified product according to the procedure described by Tettamanti et al., Biochimica et Biophysica Acta, 296 (1973) 160–170, or obtained from Fidia S.p.A., Abano Terme, Italy.

Starting from frozen cattle brains, a multistep separation procedure, based on solvent extraction, liquid/liquid partitioning, phospholipid removal by methanolysis, and molecular filtration yields a highly purified ganglioside mixture which contains ganglioside $GM_1$ in a percentage between about 18 and 24% in comparison to a reference working standard with known structure and purity. This compound is separated from the mixture by a two-step High Performance Liquid Chromatography procedure, giving a final yield of approximately 75% of the theoretical value. The obtained substance is converted to the sodium salt, dialyzed, and precipitated. The precipitate is redissolved in water, submitted to sterilizing filtration, and lyophilized. The purity of the compound obtained is more than 98% by dry weight by photodensitometry assay, in comparison to a reference working standard with known structure and purity.

Example 30

Preparation of Ganglioside Inner Ester Mixture, Sinassial

A mixture of gangliosides is obtained by extraction from bovine brains, and 5 g of this mixture are dissolved in 50 ml of dimethylsulfoxide. Then, 4 g of anhydrous styrene type resin (sultonic acid, 50–100 mesh, H$^+$ form) are added to the mixture and the resulting mixture is stirred for 30 minutes at room temperature. This treatment with an ion exchange resin converts all of the ganglioside carboxylate groups to —COOH (carboxyl) groups. Complete conversion of the carboxylate groups is confirmed by an appropriate physical analytical method, such as atomic absorption. The resin is then filtered under suction, and the solution is treated with 1.5 g of dicyclohexylcarbodiimide and allowed to stand for one hour.

The dicyclohexylurea which precipitates is removed by filtration and the remaining solution is treated with 100 ml of acetone, causing precipitation of the inner ester ganglioside derivatives. The method yields 4.6 g of inner ester product (about 90–95% of the theoretical value).

Preparation of Nerve Guide Channels

Example 31

A guide channel with a composite thread/polymeric matrix structure wherein the thread comprises HYAFF 11 (total benzyl ester of HY, 100% esterified) and the matrix is composed of HYAFF 11p75 (benzyl ester of HY 75% esterified) is obtained by the following procedure.

A thread of total HYAFP 11 esters, 250 denier, with a minimum tensile strength at break of 1.5 gr/denier and 19% elongation is entwined around an electropolished AISI 316 steel bar with an outer diameter of 1.5 mm, which is the desired inner diameter of the composite guide channel. The woven product is obtained using a machine with 16 loaders per operative part.

The system comprising the steel bar with the threaded tube fitted over it is placed in position as shown in FIG. 1. The apparatus is rotated at a speed of 115 rpm. A quantity of HYAFF 11p75/dimethylsulfoxide solution at a concentration of 135 mg/ml is spread over the rotating system. The excess solution is removed with a spatula, and the system is removed from the apparatus and immersed in absolute ethanol. After coagulation, the guide channel is removed from the steel bar and cut to size.

The channel made by the above technique is 20 mm long, 300 μm thick, has an internal diameter of 1.5 mm, and has a weight of 40 mg, equal to 20 mg/cm.

Example 32

A guide channel with a composite structure of thread/polymeric matrix, wherein the thread comprises a mixture of HYAFF 11 (80%) and HYAFF 11p75 (20%), and the matrix is composed of HYAFF 11p75, is obtained according to the following procedure.

A thread of total HYAFF 11 ester, 250 denier, with a minimum tensile strength at break of 1.5 gr/denier and 19% elongation, and a HYAFF 11p75 thread, 150 denier, minimum tensile strength at break 0.9 gr/denier and 20% elongation, are combined by means of a twisting mechanism to form a thread composed of the two products. The thread is entwined around an electropolished AISI 316 steel bar with an outer diameter of 1.5 mm, which is equal to the desired internal diameter of the composite tube. The woven product is obtained using a machine with 8 loaders per operative part.

The system comprising the steel bar with the woven tube fitted over it is placed in position on the apparatus described in FIG. 1. The apparatus is rotated at a speed of 115 rpm. A quantity of HYAFF 11p75/dimethylsulfoxide solution at a concentration of 135 mg/ml is spread over the rotating system. The excess solution is removed with a spatula, and the system is removed from the apparatus and immersed in absolute ethanol. After coagulation the guide channel is removed from the steel bar and cut to size.

The channel produced according to the above technique is 20 mm long, 400 μm thick, has an internal diameter of 1.5 mm, and weighs 30 mg, equal to 15 mg/cm.

Example 33

A guide channel with a composite structure of thread/polymeric matrix, wherein the thread comprises a mixture of total HYAFF 11 and the matrix comprises HYAFF 11p75, is obtained according to the following procedure.

A thread of total HYAFF 11 ester, 250 denier, with a minimum tensile strength at break of 1.5 gr/denier and 19% elongation, is entwined around an electropolished AISI steel bar with an outer diameter of 3 mm, which is equal to the desired internal diameter of the composite tube. The tube is woven by a machine with 16 loaders per operative part.

The system comprising the steel bar with the tube of interlaced threads around it was fitted onto the apparatus as shown in FIG. 1, but with a solution spray in the place of the loader distributing thread. The apparatus is rotated at a speed of 115 rpm. A solution of HYAFF 11p75/dimethylsulfoxide at a concentration of 135 mg/ml is distributed by activating the spray for 30 seconds as it moves along the length of the steel bar. During this time the spray moves four times along the length of the guide channel in preparation. The system is removed from the apparatus and immersed in absolute ethanol. After coagulation, the guide channel is removed from the steel bar and cut to size.

The guide channel produced according to the above procedure is 20 mm long, 180 μm thick, has an internal diameter of 3 mm, and weighs 24 mg, equal to 12 mg/cm.

Example 34

A guide channel with a composite structure of thread/polymeric matrix wherein the thread comprises total HYAFF 11, the matrix comprises HYAFF 11p75, and which contains human nerve growth factor, is obtained according to the following procedure.

A thread of total HYAFF 11 ester, 250 denier, with a minimum tensile strength at break of 1.5 gr/denier and 19% elongation, is entwined around an electropolished AISI 316 steel bar with an outer diameter of 1.5 mm, which is the desired internal diameter of the composite tube. The woven product is obtained using a machine with 16 loaders per operative part.

The system comprising the steel bar with the woven product covering it is fitted onto the apparatus shown in FIG. 1. The apparatus is rotated at a speed of 115 rpm. A quantity of a solution of HYAFF 11p75/dimethylsulfoxide at a concentration of 135 mg/ml, wherein a suitable quantity, e.g., 0.5 mg, of subunit B of human NGF has been dissolved, is spread onto the rotating system.

The excess solution is removed with a spatula, and the system is removed from the apparatus and immersed in absolute ethanol. After coagulation, the guide channel is removed from the steel bar and cut to size.

The guide channel made according to the above technique is 20 mm long, 300 μm thick, has an internal diameter of 1.5 mm, and weights 40 mg, equal to 20 mg/cm.

Example 35

A guide channel with a composite structure of thread/polymeric matrix wherein the thread comprises total HYAFF 11, the matrix comprises HYAFF 11p75, and which contains CNTF growth factor, is obtained according to the following method.

A thread of total HYAFF 11 ester, 250 denier, with a minimum tensile strength at break of 1.5 gr/denier and 19% elongation, is entwined around an electropolished AISI 316 steel bar with an external diameter of 1.5 mm, which is the desired internal diameter of the composite guide channel. The woven product is obtained using a machine with 16 loaders per operative part.

The system comprising the steel bar and the threaded tube is placed on the apparatus as shown in FIG. 1. The apparatus is rotated at a speed of 115 rpm. A quantity of HYAFF 11p75/dimethylsulfoxide solution at a concentration of 135 mg/ml, in which a suitable quantity, e.g., 0.5 mg, of CNTF growth factor has been dissolved, is spread Con the rotating system. Any excess solution is removed with a spatula, and the system is removed from the apparatus and immersed in absolute ethanol. After coagulation the guide channel is removed from the steel bar and cut to size.

The guide channel produced according to the above technique is 20 mm long, 300 μm thick, has an internal diameter of 1.5 mm, and weighs 40 mg, equal to 20 mg/cm.

Example 36

A guide channel with a composite structure of thread/polymeric matrix wherein the thread comprises a mixture of total HYAFF 11 containing a suitable quantity of the growth factor BDNF, and the matrix comprises HYAFF 11 p75, is obtained according to the following procedure.

A thread of total HYAFF 11 ester, 250 denier, with a minimum tensile strength at break of 1.5 gr/denier and 19% elongation, is entwined around an electropolished AISI 316 steel bar with an external diameter of 3 mm, which is the desired internal diameter of the composite guide channel. The woven product is obtained using a machine having 16 thread loaders per operative part.

The system comprising the steel bar covered by the woven tube is fitted onto the apparatus as shown in FIG. 1, where a solution spray has been fixed in place of the thread loader. The apparatus is rotated at a speed of 115 rpm. The solution of HYAFF 11p75/dimethylsulfoxide at a concentration of 135 mg/ml, wherein a suitable quantity, e.g., 0.5 mg, of the growth factor BDNF has been dissolved, is sprayed onto the tube for 30 seconds while the spray moves back and forth along the steel bar.

During this time the spray travels the length of the guide channel four times. The system is then removed from the apparatus and immersed in absolute ethanol. After coagulation the guide channel is removed from the steel bar and cut to size.

The guide channel produced according to the above technique is 20 mm long, 180 μm thick, has an internal diameter of 3 mm, and weighs 24 mg, equal to 12 mg/cm.

Example 37

A guide channel with a composite structure of thread/polymeric matrix wherein the thread comprises total HYAFF 11, the matrix comprises HYAFF 11p75, and which contains a suitable quantity of ganglioside mixture Cronassial, is obtained according to the following method.

A thread of total HYAFF 11 ester, 250 denier, with a minimum tensile strength at break of 1.5 gr/denier and 19% elongation, is entwined around an electropolished AISI steel bar with an external diameter of 1.5 mm, which is the desired internal diameter of the composite tube. The woven product is obtained using a machine having 16 thread loaders per operative part.

The system comprising the steel bar covered with the woven tube is mounted onto the apparatus shown in FIG. 1. The apparatus is rotated at a speed of 115 rpm. The rotating system is coated with a quantity of a solution of HYAFF 11p75/dimethylsulfoxide at a concentration of 135 mg/ml, wherein a suitable quantity, e.g., 20 mg, of ganglioside mixture Cronassial has been dissolved.

The excess solution is removed with a spatula, and the system is removed from the apparatus and immersed in absolute ethanol. After coagulation, the guide channel is removed from the steel bar and cut to size.

The guide channel produced according to the above technique is 20 mm long, 300 μm thick, has an internal diameter of 1.5 mm, and weighs 40 mg, equal to 20 mg/cm.

Example 38

A guide channel with a composite structure of thread/polymeric matrix wherein the thread comprises a mixture of total HYAFF 11 containing a suitable quantity of monosialoganglioside fraction GM1, Sygen, and the matrix comprises HYAFF 11p75, is obtained according to the following procedure.

A thread of total HYAFF 11, 250 denier, with a minimum tensile strength at break of 1.5 gr/denier and 19% elongation, is entwined around an electropolished AISI 316 steel bar with an external diameter of 3 mm, which is the desired internal diameter of the composite tube. The woven product is obtained using a machine having 16 loaders per operative part.

The system comprising the steel bar with the threaded tube around it is mounted onto the apparatus shown in FIG. 1, with a solution spray mounted in the place of the thread loader. The apparatus is rotated at a speed of 115 rpm. A solution of HYAFF 11p75/dimethylsulfoxide at a concentration of 135 mg/ml, wherein a suitable quantity, e.g., 20 mg, of the monosialoganglioside fraction GM1 known as Sygen has been dissolved, is distributed by activating the spray for 30 seconds as it moves up and down the length of the steel bar. During this time, the spray travels the length of the bar four times. The system is removed from the apparatus and immersed in absolute ethanol. After coagulation the guide channel is removed from the steel bar and cut to size.

The guide channel produced according to the above technique is 20 mm long, 180 μm thick, has an internal diameter of 3 mm, and weighs 24 mg, equal to 12 mg/cm.

Example 39

A guide channel with a composite structure of thread/polymeric matrix wherein the thread comprises a mixture of total HYAFF 11 containing a suitable quantity of semisynthetic ganglioside mixture Sinassial, and the matrix comprises HYAFF 11p75, is obtained according to the following method.

A thread of total HYAFF 11, 250 denier, with a minimum tensile strength at break of 1.5 and 19% elongation, is entwined around an electropolished AISI 316 stool bar with an external diameter of 3 mm, which is the desired internal diameter of the composite guide channel. The woven product is obtained using a machine having 16 loaders per operative part.

The system comprising the steel bar covered by the interwoven tube is mounted onto the apparatus in. FIG. 1, with a solution spray mounted in the place of the thread loader. The apparatus is rotated at a speed of 115 rpm. The solution of HYAFF 11p75/dimethylsulfoxide at a concentration of 135 mg/ml, wherein a suitable quantity, e.g., 20 mg, of ganglioside mixture Sinassial has been dissolved, is distributed by activating the spray for 30 seconds as it moves up and down the length of the steel bar. During this time, the spray travels the length of the bar four times. The system is removed from the apparatus and immersed in absolute ethanol. After coagulation, the guide channel is removed from the steel bar and cut to size.

The guide channel produced according to the above technique is 20 mm long, 180 μm thick, has an internal diameter of 3 mm, and weighs 24 mg, equal to 12 mg/cm.

The guide channels produced according to the present invention can be used, for example, as guides for peripheral nerve regeneration (see Example 40) or as adjuvants in peripheral nerve neurorrhaphy (see Example 41). With specific reference to the former use, these guide channels can be fixed to the stumps of the damaged nerves by suture threads, without thereby prejudicing the function of the guide or its ability to guide axonal growth along its interior.

To illustrate the use of the guide channels of the present invention, and to demonstrate their function and bioabsorbability, the following tests were performed.

Example 40

Ten rats, each weighing 250–300 gr, whose sciatic nerves had been cut in the median part, were used. Two mm of nerve were removed so that an 8 mm gap was left after spontaneous shrinkage. Both stumps, proximal and distal, were inserted into a guide channel (described in Example 34) which had been filled with saline. The guide was fixed in place with a nylon suture thread (9–0). The guide channel proved to be intact after suture. 90 days after surgery, the function of the regenerated nerve was tested. The results showed that the guide channel produced according to the present invention was able to enhance and guide axonal growth.

Figure 2:
FIG. 2 shown the reabsorption in vivo of the composite guide channel used in Example 10 ten days after implant.
Figure 3:
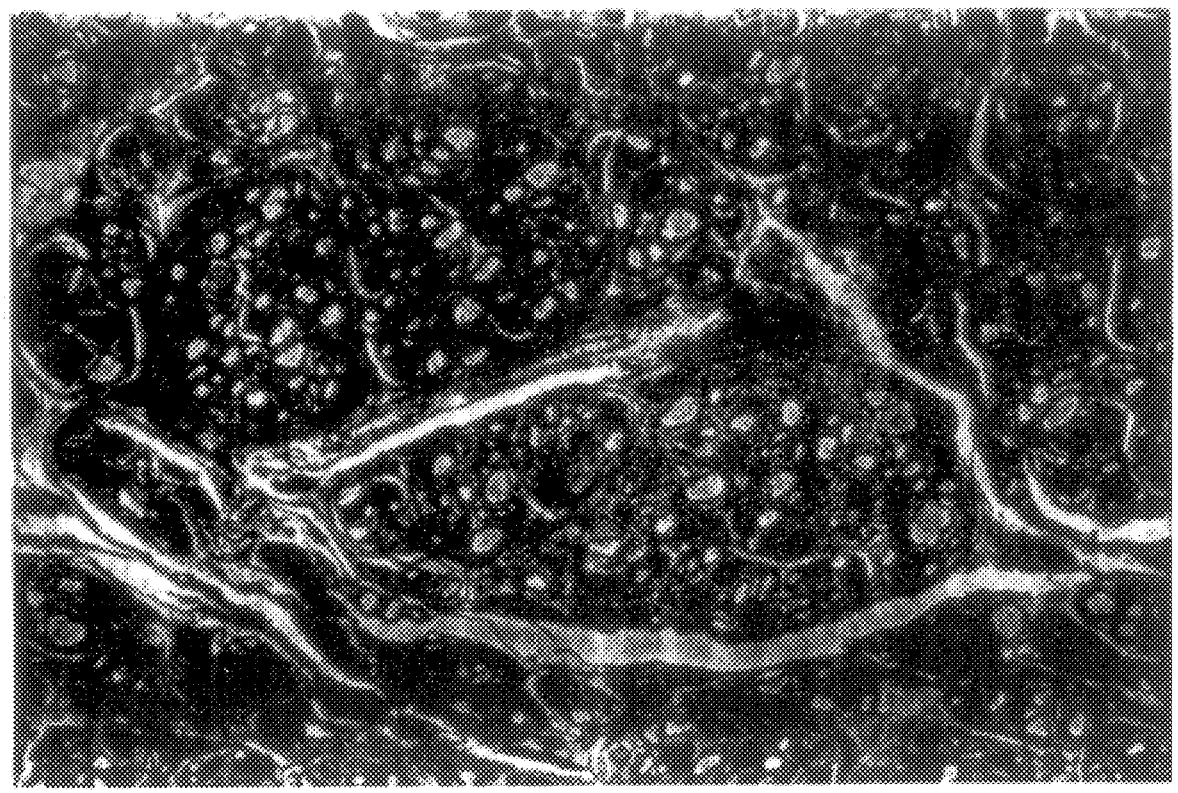
FIG. 3 shows the axonal regeneration of the damaged nerve four weeks after implant of the composite guide channel used in Example 10.

Further investigations on the regenerated nerves demonstrated the bioabsorbability of the guide channels used (FIG. 2), and consequent recovery of nervous unction (FIG. 3).

Example 41

Guide channels were used as adjuvants in peripheral nerve neurorrhaphy in an allograft experiment in rats. This surgical technique is particularly interesting and can be applied to advantage for the following reasons:

i) it reduces the amount of suture material needed, which usually remains unabsorbed round the reconnected site;

ii) it provides a barrier against cellular elements such as fibroblasts, which are foreign to the nerve itself; and iii) it allows grafts of different sizes from the damaged nerve to reconnect, thanks to the use of cone-shaped guide channels.

The experiments designed to assess the function and bioabsorbability of the guide channels of the present invention (in particular the guide channel described in Example 31) were performed in consanguineous rats weighing about 300 gr. Allograft was effected according to the described technique. The sciatic nerve of the receiver rat was cut to create a gap of about 15 mm. The sciatic nerve of the donor rat was placed in the gap without using sutures, but by holding the damaged nerve and the graft together inside the guide channel. The graft was then sewn to the guide channel, without leaving any gap, with two epineural stitches.

Figure 4:
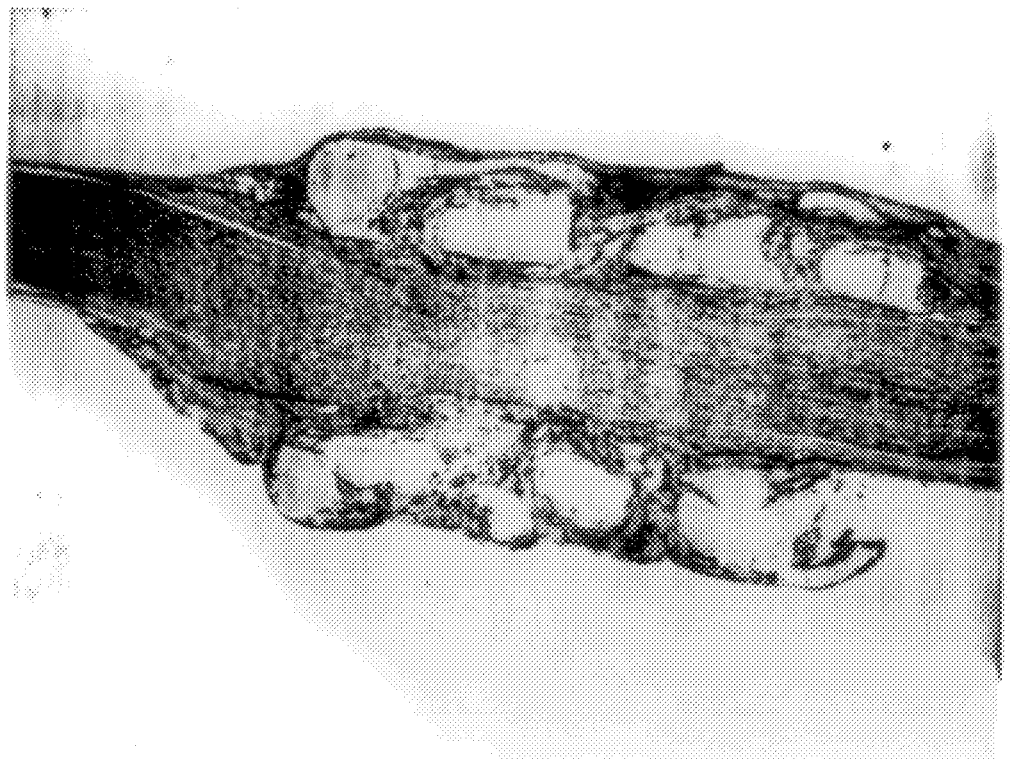
FIG. 4 shows the reconnection or the nerve in peripheral nerve neurorraphy by use of the guide channel in Example 11. Histological observation was performed 20 days after surgery.
Figure 5:
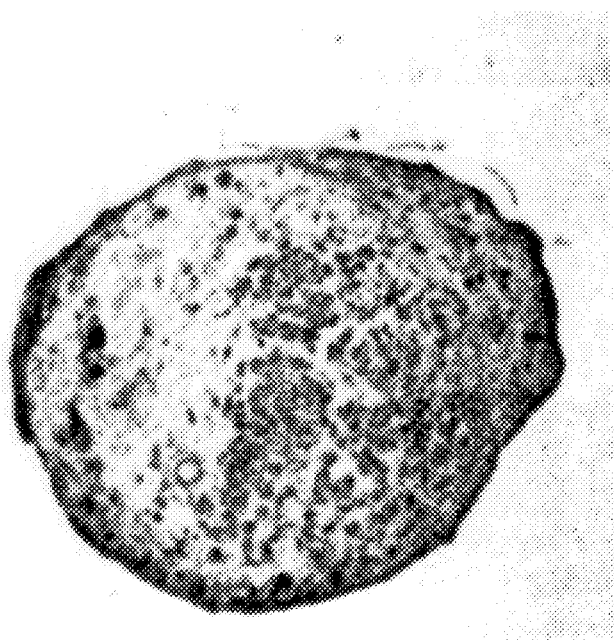
FIG. 5 shows the presence of regenerated axons at the level of the graft obtained by use of the guide channel in Example 11. The presence of axons was demonstrated by the use of antineurofilament antibodies. Observation was performed 20 days after surgery.

The preliminary results obtained in groups of 10 rats which had undergone neurorrhaphy showed excellent reconnection of the nerve (FIG. 4), and the presence of regenerated axons at the level of the graft (FIG. 5) after 20 days, by which time the guide channel had been almost completely absorbed. Moreover, the experiment showed that the guide channel is able to prevent the formation of adherences.

Applications of the Present Guide Channels

The composite guide channels of the present invention can be employed as medical devices for peripheral nerve regeneration, particularly in the microsurgery of the hand to restore the continuity of the nerve interrupted by traumatic events or surgical procedures, and in the treatment of damaged tendons, specifically in plastic surgery to restore tendon function derived from tenorrhaphy, and particularly in surgery of the hand and foot following traumatic events or surgical procedures.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims:

What is claimed:

1. A medical device for use in the treatment of damaged nerve tissue, said device comprising a tubular, biocompatible and bioabsorbable composite, which comprises:

a matrix comprising a biocompatible, bioabsorbable, water-insoluble ester of hyaluronic acid;

a tubular reinforcement structure comprising interlaced threads comprising a biocompatible, bioabsorbable, water-insoluble ester of hyaluronic acid.

2. The medical device according to claim 1, wherein said ester of hyaluronic acid is a total or partial ester of hyaluronic acid with a pharmacologically inactive alcohol.

3. The medical device according to claim 2, wherein said alcohol is an aliphatic, araliphatic, cycloaliphatic, or heterocyclic alcohol.

4. The medical device according to claim 3, wherein said aliphatic alcohol is a $C_{1-12}$ aliphatic alcohol.

5. The medical device according to claim 3, wherein said aliphatic alcohol is benzyl alcohol.

6. The medical device according to claim 1, wherein said ester is a total ester of hyaluronic acid.

7. The medical device according to claim 1, wherein said ester is a partial ester of hyaluronic acid.

8. The medical device according to claim 1, wherein said ester of hyaluronic acid is an ester of hyaluronic acid 75% esterified with benzyl alcohol.

9. The medical device according to claim 1, wherein said interlaced threads have a denier in the range of from about 120 denier to about 600 denier, a tensile strength at break in the range of from about 0.6 gr/denier to about 3.5 gr/denier; a minimum elongation in the range of from about 3% to about 10%, and a number of threads in the range of from about 8 to about 16.

10. The medical device according to claim 9, wherein said device has a length in the range of from about 5 to about 150 mm, an internal diameter in the range of from about 1 to about 15 mm, a thickness in the range of from about 50 μm to about 1,000 μm, and a weight in the range of from about 8 mg to about 80 mg, corresponding to 4 to 40 mg/cm.

11. The medical device according to claim 10, wherein said device has a length of 20 mm, an internal diameter of 1.5 to 3 mm, a thickness of 400 μm, and a weight of 20 mg, corresponding to 10 mg/cm.

12. The medical device of claim 1 further comprising at least one biologically or pharmacologically active molecule wherein said biologically or pharmacologically active molecule is a molecule that increases and/or stimulates the growth, regeneration, and/or repair of damaged tissues.

13. The medical device according to claim 12, wherein said biologically or pharmacologically active molecule is at least one member selected from the group consisting of nerve growth factor, basic fibroblast growth factor in its acid or basic forms, ciliary neuronotrophic factor, biologically active truncated ciliary neuronotrophic factor, brain-derived neurotrophic factor, neurotrophin-3, neurotrophin-4, a ganglioside, a ganglioside derivative, a ganglioside mixture, a mixture of ganglioside derivatives, and a mixture of any of the foregoing.

14. Use of the medical device according to claim 12 in surgery and microsurgery.

15. The use according to claim 14, wherein said medical device is employed at anatomical sites where conditions of discontinuity and/or loss of substance have occurred.

16. The use according to claim 15, wherein the anatomical site is a damaged peripheral nerve or a damaged tendon.

17. The use according to claim 16, wherein said medical device is used for nerve regeneration or as an adjuvant in neurorrphaphy.

18. The use according to claim 15, wherein said medical device is employed to prevent post-operative adherences and their recurrence.

19. The medical device according to claim 12, the preparation of which includes the co-extrusion of said at least one biologically or pharmacologically active molecule with said threads comprising said tubular reinforcing structure.

20. A process for preparing the medical device according to claim 1, comprising coating said tubular reinforcement structure comprising interlaced threads comprising a biocompatible, bioabsorbable, water-insoluble ester of hyaluronic acid with a solution of a biocompatible, bioabsorbable, water-insoluble ester of hyaluronic acid, using an electropolished steel cylinder holding the rotating tubular reinforcement structure rotating at a minimum of 100 rpm.

21. The process according to claim 20, wherein said coating is performed by spraying said solution.

22. The process of claim 20 wherein said solution further comprises at least one biologically or pharmacologically active molecule.

* * * * *